(12) United States Patent
Christiansen et al.

(10) Patent No.: US 10,624,795 B2
(45) Date of Patent: Apr. 21, 2020

(54) SENSOR FOR ABSORBENT ARTICLE

(71) Applicant: Medline Industries, Inc., Mundelein, IL (US)

(72) Inventors: Michelle Christiansen, McHenry, IL (US); Jeremy Stephen Fogel, Evanston, IL (US); William Bowser, Mundelein, IL (US)

(73) Assignee: Medline Industries, Inc., Northfield, IL (US)

( * ) Notice: Subject to any disclaimer, the term of this patent is extended or adjusted under 35 U.S.C. 154(b) by 484 days.

(21) Appl. No.: 15/626,729

(22) Filed: Jun. 19, 2017

(65) Prior Publication Data

US 2017/0360623 A1   Dec. 21, 2017

Related U.S. Application Data

(60) Provisional application No. 62/351,372, filed on Jun. 17, 2016.

(51) Int. Cl.
*A61F 13/42* (2006.01)
*G01N 27/04* (2006.01)

(52) U.S. Cl.
CPC .......... *A61F 13/42* (2013.01); *G01N 27/048* (2013.01); *A61F 2013/424* (2013.01)

(58) Field of Classification Search
CPC combination set(s) only.
See application file for complete search history.

(56) References Cited

U.S. PATENT DOCUMENTS

| 4,834,733 A | 5/1989 | Huntoon |
| 5,266,928 A | 11/1993 | Johnson |

(Continued)

FOREIGN PATENT DOCUMENTS

| WO | 2002078513 A2 | 10/2002 |
| WO | 2004021944 A1 | 3/2004 |

(Continued)

OTHER PUBLICATIONS

Notification of Transmittal of the International Search Report and the Written Opinion of the International Searching Authority, or the Declaration; International Application No. PCT/US2018/021070; Medline Industries, Inc. (Love), Jul. 5, 2018.

(Continued)

*Primary Examiner* — Travis R Hunnings
(74) *Attorney, Agent, or Firm* — Robert D. Spendlove; Gurr Brande & Spendlove, PLLC

(57) ABSTRACT

A sensor for monitoring wetness in a diaper or other absorbent article includes a housing that attaches to the absorbent article. The sensor may include inner and outer housing portions that capture an edge of the absorbent article between the housings. The sensor may include contacts that electrically connect with a pair of contact strips embedded in the absorbent article. The distance between the embedded strips may vary depending on the size of the absorbent article. The sensor may include multiple pairs of contacts that are spaced apart to match the distance between the contact strips for the variously sized absorbent articles. In this way, depending on the pair of contacts connected to the contact strips, the sensor may indicate the size of the absorbent article.

20 Claims, 5 Drawing Sheets

(56) References Cited

U.S. PATENT DOCUMENTS

| | | | |
|---|---|---|---|
| 5,291,181 | A | 3/1994 | DePonte |
| 5,443,082 | A | 8/1995 | Mewburn |
| 5,459,452 | A * | 10/1995 | DePonte ............... A61F 13/42 |
| | | | 128/886 |
| 5,469,145 | A | 11/1995 | Johnson |
| 5,570,082 | A | 10/1996 | Mahgerefteh |
| 5,796,345 | A | 8/1998 | Leventis |
| 5,838,240 | A | 11/1998 | Johnson |
| 5,868,723 | A | 2/1999 | Al-Sabah |
| 6,097,297 | A | 8/2000 | Fard |
| 6,373,395 | B1 | 4/2002 | Kimsey |
| 6,384,728 | B1 | 5/2002 | Kanor |
| 6,559,772 | B2 | 5/2003 | Zand |
| 6,583,722 | B2 | 6/2003 | Jeutter |
| 6,603,403 | B2 | 8/2003 | Jeutter |
| 6,617,488 | B1 | 9/2003 | Springer |
| 6,756,521 | B1 | 6/2004 | Breitkopf |
| 6,774,800 | B2 | 8/2004 | Friedman |
| 6,870,479 | B2 | 3/2005 | Gabriel |
| 6,970,091 | B2 | 11/2005 | Roe |
| 7,053,781 | B1 | 5/2006 | Haire et al. |
| 7,295,125 | B2 | 11/2007 | Gabriel |
| 7,321,315 | B2 | 1/2008 | Brumm |
| 7,352,286 | B2 | 4/2008 | Chan |
| 7,355,090 | B2 | 4/2008 | Ales |
| 7,394,391 | B2 | 7/2008 | Long |
| 7,477,156 | B2 | 1/2009 | Long |
| 7,498,478 | B2 | 3/2009 | Long |
| 7,642,396 | B2 | 1/2010 | Ales |
| 7,649,125 | B2 | 1/2010 | Ales |
| 7,956,754 | B2 | 6/2011 | Long |
| 7,977,529 | B2 | 7/2011 | Bergman |
| 8,032,426 | B2 | 10/2011 | Williams |
| 8,101,813 | B2 | 1/2012 | Ales |
| 8,112,322 | B2 | 2/2012 | Williams |
| 8,190,495 | B1 | 5/2012 | Williams |
| 8,196,809 | B2 | 6/2012 | Thorstensson |
| 8,237,572 | B2 | 8/2012 | Clement |
| 8,248,249 | B2 | 8/2012 | Clement |
| 8,274,393 | B2 | 9/2012 | Ales |
| 8,314,284 | B1 | 11/2012 | Novello |
| 8,376,232 | B2 | 2/2013 | Eckstein |
| 8,378,167 | B2 | 2/2013 | Allen |
| 8,421,636 | B2 | 4/2013 | Collette |
| 8,471,715 | B2 | 6/2013 | Solazzo |
| 8,604,268 | B2 | 12/2013 | Cohen |
| 8,697,933 | B2 | 4/2014 | Ales |
| 8,698,641 | B2 | 4/2014 | Abraham |
| 8,866,624 | B2 | 10/2014 | Ales |
| 8,871,994 | B2 | 10/2014 | Wei |
| 8,884,769 | B2 | 11/2014 | Novak |
| 8,962,909 | B2 | 2/2015 | Groosman |
| 8,978,452 | B2 | 3/2015 | Johnson |
| 9,107,776 | B2 | 8/2015 | Bergman |
| 9,132,044 | B2 | 9/2015 | Sjöholm |
| 9,138,354 | B2 | 9/2015 | Nhan |
| 9,160,054 | B2 | 10/2015 | Yu |
| 9,194,833 | B2 | 11/2015 | Bosaeus |
| 9,224,102 | B2 | 12/2015 | Barda |
| 9,241,839 | B2 | 1/2016 | Abraham |
| 9,278,033 | B2 | 3/2016 | Abraham |
| 9,283,123 | B2 | 3/2016 | Lewis |
| 9,314,381 | B2 | 4/2016 | Curran |
| 9,322,797 | B1 | 4/2016 | Lastinger |
| 9,366,644 | B1 | 4/2016 | Lastinger |
| 9,333,118 | B2 | 5/2016 | Elfström |
| 2003/0060789 | A1 * | 3/2003 | Shapira ............... A61F 13/42 |
| | | | 604/361 |
| 2004/0030309 | A1 * | 2/2004 | Huang ............... A61F 13/15585 |
| | | | 604/361 |
| 2004/0078014 | A1 * | 4/2004 | Shapira ............... A61F 13/42 |
| | | | 604/361 |
| 2004/0100376 | A1 | 5/2004 | Lye |
| 2004/0113801 | A1 * | 6/2004 | Gustafson ........... A61F 13/2051 |
| | | | 340/604 |
| 2004/0230172 | A1 * | 11/2004 | Shapira ............... A61F 13/42 |
| | | | 604/361 |
| 2010/0089264 | A1 | 4/2010 | Warner |
| 2010/0168694 | A1 | 7/2010 | Gakhar |
| 2012/0161960 | A1 | 6/2012 | Cheng |
| 2012/0172825 | A1 | 7/2012 | Ales |
| 2012/0173249 | A1 | 7/2012 | Popp |
| 2013/0052432 | A1 | 2/2013 | Koebel |
| 2013/0345657 | A1 | 12/2013 | Nelson |
| 2014/0063085 | A1 | 3/2014 | Warner |
| 2015/0080819 | A1 | 3/2015 | Charna et al. |
| 2016/0267769 | A1 | 9/2016 | Rokhsaz et al. |
| 2018/0256412 | A1 * | 9/2018 | Love ............... A61F 13/53 |

FOREIGN PATENT DOCUMENTS

| | | |
|---|---|---|
| WO | 2006058276 A2 | 6/2006 |
| WO | 2007125446 A1 | 11/2007 |
| WO | 2008130298 A1 | 10/2008 |

OTHER PUBLICATIONS

Notification of Transmittal of the International Search Report and the Written Opinion of the International Searching Authority, or the Declaration; International Application No. PCT/US2017/038146; Medline Industries, Inc. (Christiansen), Oct. 30, 2017.

* cited by examiner

SENSOR FOR ABSORBENT ARTICLE

FIELD OF THE INVENTION

The present invention relates generally to absorbent articles and, in particular, to the use of wetness sensors.

BACKGROUND

Millions of people of all ages suffer from incontinence of the bowel or bladder. Whether an infant, adult, or elderly person, the underlying cause of incontinence varies but the method of treatment typically involves absorbent article products. Adult incontinent briefs, disposable diapers, pull-up diapers, protective underwear and underpads can alleviate some of the emotional and physical discomfort of incontinence by absorbing and containing liquid and other discharges from the human body to prevent body and clothing soiling.

Typical absorbent articles include a topsheet facing the wearer that permits fluid exudates to pass through and a backsheet that prevents the exudates from escaping from the absorbent article. Much advancement has been made in the art since the introduction of the disposable absorbent article, as shown, for example, in applicant's co-pending U.S. patent application Ser. No. 13/832,965, which is incorporated by reference herein. However, quality care for patients and other users of absorbent articles requires that the article be changed after being wetted, and most of these articles are not adapted to aid the caregiver in the monitoring of the status of the article.

A number of devices and wetness detecting systems have been attempted to report when a diaper, bedding, or adult incontinence article becomes wet due to incontinence. For example, U.S. Pat. No. 8,421,636, which is incorporated herein by reference, describes a patient monitoring system that detects wetness in an absorbent article. However, such devices may be improved in various ways as set forth herein.

BRIEF DESCRIPTION OF THE DRAWINGS

Advantages of the invention will become apparent upon reading the following detailed description and upon reference to the drawings.

Figure 1:
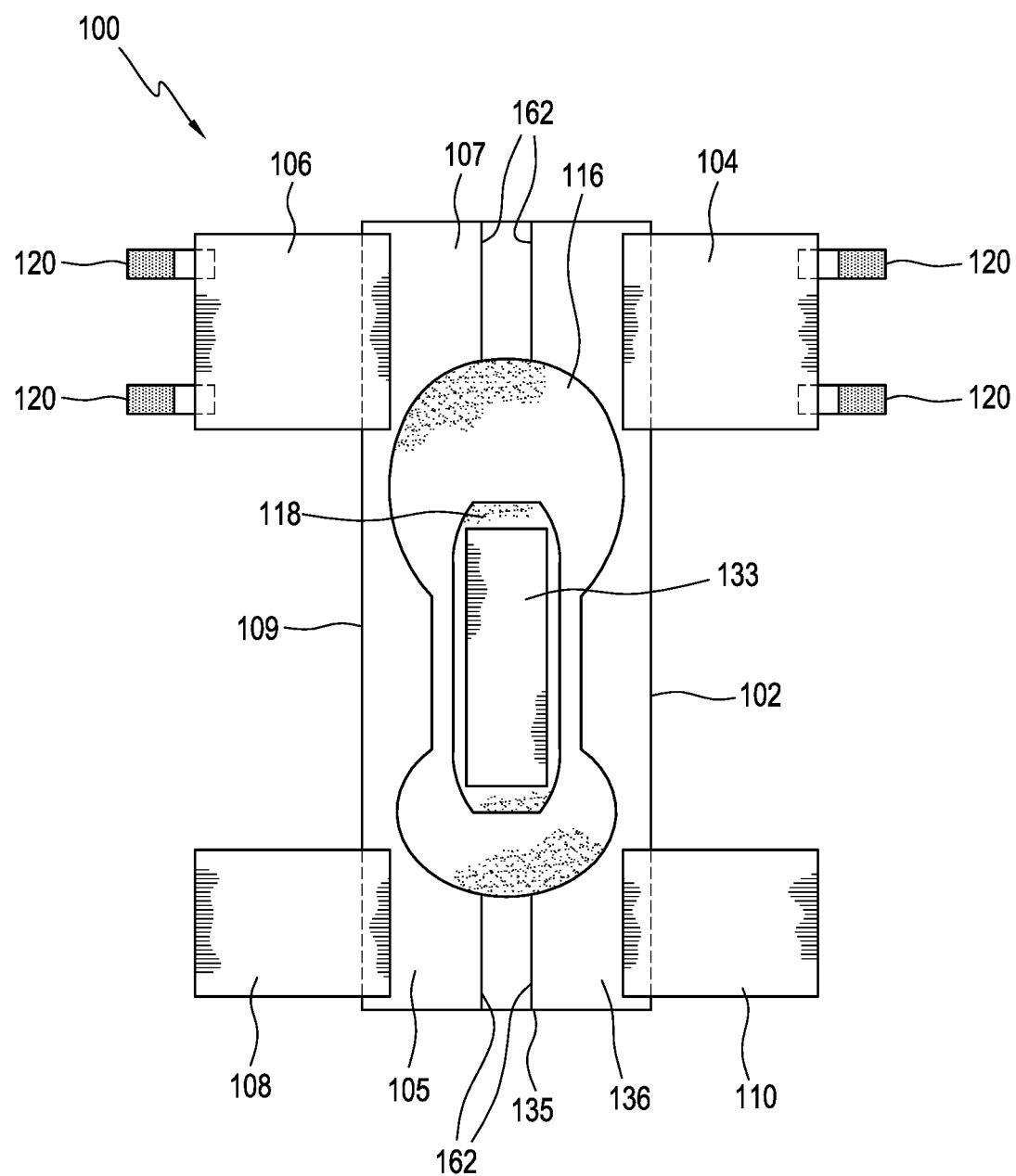
FIG. 1 is a top plan view of an absorbent article in a substantially flat un-contracted position according to one embodiment of the invention.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, forward and rearward, and the like may be used solely to distinguish one entity or action from another entity or action without necessarily requiring or implying any actual such relationship, direction or order between such entities or actions.

Absorbent articles as described herein generally include a moisture-pervious inner layer, an absorbent layer, and a moisture-impervious outer layer. Although the remainder of the description will be specifically directed to adult incontinence articles, such as disposable diapers, it is to be understood that the embodiments may also be implemented using other absorbent articles and that the properties and uses described below apply to these other absorbent articles as well. Throughout this application, the terms absorbent article and diaper are used interchangeably. However, it should be understood that the term diaper is intended to include other absorbent articles, such as training pants, incontinence pads, etc., as would be understood by one of ordinary skill in the art. The terms user and patient are also used interchangeably to indicate a person on whom a diaper is placed.

Figure 2:
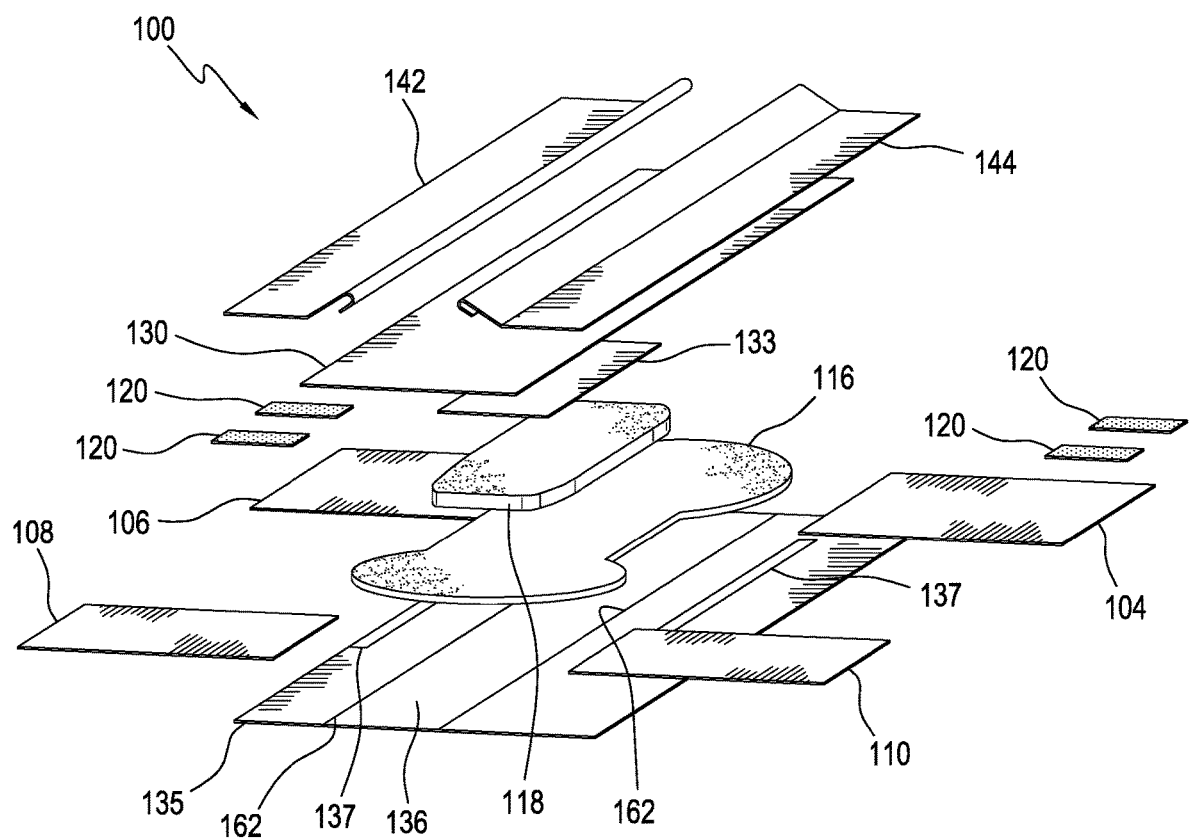
FIG. 2 is an exploded perspective view of the absorbent article of FIG. 1, again in a substantially flat un-contracted position.

FIGS. 1 and 2 illustrate an exemplary non-limiting general embodiment of an absorbent article 100. FIG. 1 illustrates a plan view of the absorbent article 100 in a substantially flat un-contracted state. As shown in these figures, the absorbent article 100 generally consists of several layers, including an inner layer, an absorbent layer, and an outer layer. The inner layer faces a wearer and contacts the skin of the wearer when the absorbent article 100 is secured to the wearer. The inner layer may comprise a topsheet 130 that is composed of a moisture-pervious fabric suitable to allow bodily discharge to pass through the inner layer and be absorbed by the absorbent layer. Non-limiting examples of materials suitable to form the topsheet 130 include polypropylene, polyethylene, polyester, materials having hydrophobic properties, combinations thereof and/or the like. Additionally, the topsheet can be treated with a hydrophilic finish to improve pass through of liquids to diaper layers beneath the inner layer. Non-limiting examples of suitable hydrophilic finishes include stearic acid, melamine-based chemicals, fluorocarbon chemicals, and silicon based chemicals.

The plan view of FIG. 1 is shown from the top or patient contacting side of the absorbent article. The topsheet (130) and other components have been removed for clarity. FIG. 2 is an exploded perspective view of the absorbent article 100. Again, the article 100 is shown in a substantially flat un-contracted state with certain items removed for clarity.

As shown in FIG. 1, an embodiment of the absorbent article 100 comprises a chassis 102. The chassis 102 includes a front waist region 105, a back waist region 107, and a crotch region 109 that is disposed longitudinally between the front and back waist regions 105 and 107. The front waist region 105 and the back waist region 107 generally comprise those portions of the absorbent article 100 which, when worn, encircle the waist of the wearer. The crotch region 109 is that portion of the absorbent article 100 which, when the absorbent article 100 is worn, is generally positioned between the legs of the wearer.

The chassis 102 has a shape such that its outer perimeter is rectangular or at least substantially rectangular in the illustrative embodiment of the absorbent article 100. In other embodiment, there may be portions of the chassis that are shaped and/or removed, such as in the crotch region 109, for example, resulting in a narrower crotch region portion 109 to provide a contoured fit between the legs. Still other embodiments have different shaped chassis, such as hour-glass shapes, T-shapes, and the like.

Rear side panels 104, 106 are coupled to and may extend from the back waist region 105. The disposable article may further include front side panels 108, 110 that are coupled to and may extend from the front waist region 105. The back region 107 is generally positioned against the back of the user. The front region 105 is generally positioned against the front of the user. The rear side panels 104, 106 are configured to wrap around a wearer's waist from back to front, extending from each side of the back waist region 105. The front side panels 108, 110 are configured to wrap around a wearer's waist from front to back. In this manner, rear side panel 106 can be connected to front side panel 108 and rear side panel 104 can be connected to front side panel 110 to couple the front region 105 to the back region 107. In this embodiment there are four side panels 104, 106, 108, 110. However, it should be recognized that other embodiments may be configured with more or fewer side panels. In particular, rear side panels 104, 106 may connect directly to an outside surface of front waist region 105 rather than to front side panels 108, 110.

The side panels may attach to the chassis 102 in a variety of manners as would be apparent to one of skill in the art. For example, as described in applicant's co-pending U.S. patent application Ser. No. 13/832,965. Alternatively, one or more of the side panels may be integrally formed, in whole or in part, with a backsheet 135 or topsheet 130 of the absorbent article. The backsheet 135 will have an outside surface 134 facing away from the patient wearing the absorbent article and an inside surface 136 facing toward the patient.

The rear side panels 104, 106 may also include fasteners 120. Fasteners 120 may comprise adhesive tape, hook and loop, snaps or any other appropriate fasteners as would be understood by one of ordinary skill in the art. As shown in the illustrative embodiment, rear side panel 104, 106 includes two fasteners 120. In a preferred embodiment, fasteners 120 can be configured to operatively couple rear side panels 104, 106 to a front region 105 of the diaper chassis 102. Alternative, fasteners 120 may also engage front side panels 108, 110 to attach rear side panels 104, 106, respectively. While FIG. 1 depicts rear side panels 104, 106 as including two fasteners 120, in some embodiments, more or fewer fasteners may be used. While FIG. 1 depicts fasteners 120 sized and shaped a particular way, in other embodiments, fasteners 120 can be a different size and/or shape. Alternatively, the front side panels 108, 110 may include fasteners in additions to, or in place of, the fasteners 120 attached to rear side panels 104, 106.

In another embodiment, the front region 105 and/or front panels 108, 110 may include added or modified features to reinforce or increase the affinity to the fastening device. Additionally, features may be employed to allow adhesive fasteners to be attached and detached from the fastening region multiple times. Those skilled in the art will recognize that there are multiple approaches to doing so via modification of the base material as well as additions of various materials. For example, fasteners 120 may incorporate the hook component of a hook-and-loop closure and portions of the front region 105 and/or front panels 108, 110 may be comprise a corresponding loop component. The surface of front region 105 and/or front panels 108, 110 may be treated to increase or decrease the affinity for the hook components. Alternatively, separate loop component material may be adhered to the surface of the front region 105 and/or front panels 108, 110.

Referring again FIGS. 1 and 2, embodiments of the absorbent article 100 include an absorbent layer. The absorbent layer may comprise an acquisition and/or distribution ("A/D") layer 133, a first absorbent core 116, and a second absorbent core 118.

The liquid acquisition and/or distribution layers serves to rapidly acquire and then distribute acquired liquid to an absorbent core for retention. To achieve rapid acquisition and distribution, these layers often include cellulosic fibers. These layers can include cross-linked cellulosic fibers to impart bulk and resilience to the layer, and wood pulp fibers to increase the wicking of liquid within the layer and to facilitate distribution of the liquid throughout the layer and ultimately to another layer, such as a storage layer, that is in liquid communication with the distribution layer.

Figure 3:
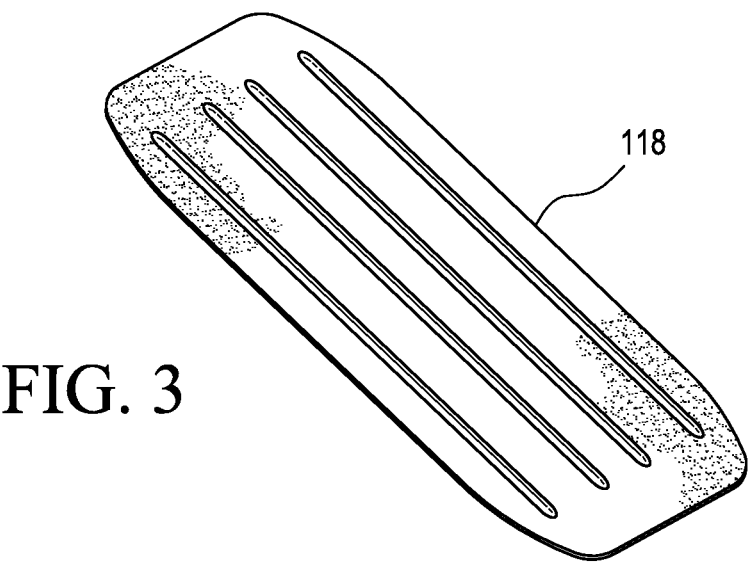
FIG. 3 is a perspective view of a second absorbent core of the absorbent article depicted in FIG. 1.
Figure 4:
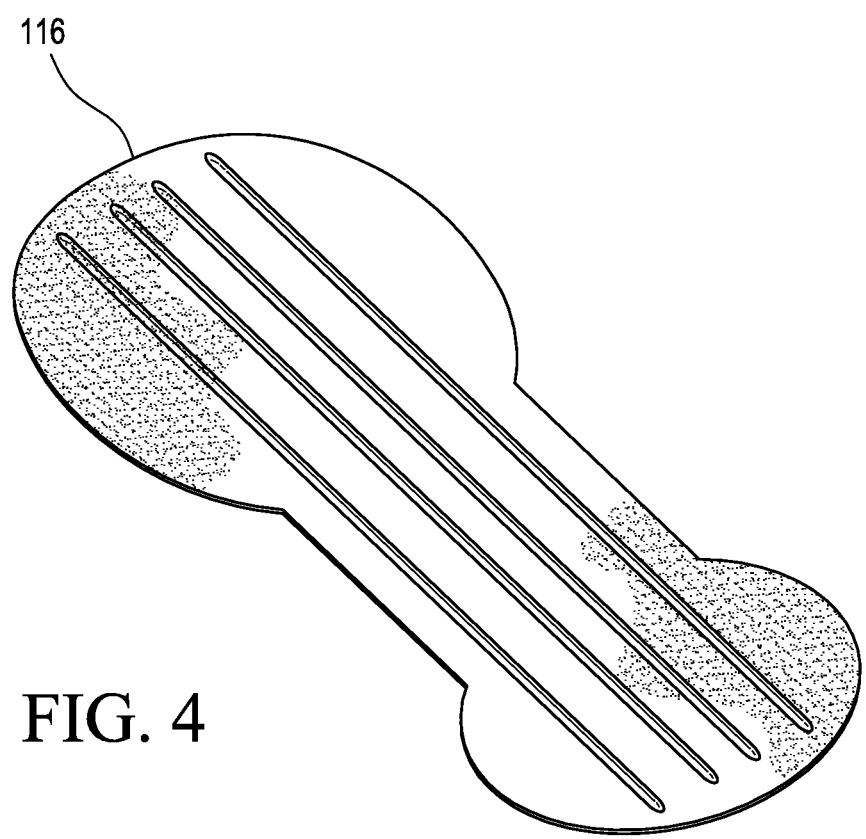
FIG. 4 is a perspective view of a first absorbent core of the absorbent article depicted in FIG. 1.

FIG. 3 is a perspective view of a top (facing towards wearer) of the second core 118, and FIG. 4 is a perspective view of a bottom side (facing away from a wearer) of the first core 116. Each of the first core 116 and second core 118 can be composed of similar material, and can be shaped depending on the size of the absorbent article, and whether it is intended for use by infants, children and/or adults. By way of example, and as shown in FIGS. 3 and 4, first core 116 can be larger and substantially hourglass shaped, whereas second core 118 can be smaller, relative to first core 116, and can be substantially rectangular shaped. In this manner, the absorbent article can include a large surface area of coverage provided by the first core 116, and the increased absorbency provided by the second core 118, without the additional bulk of a second core having the same size as the first core.

First core 116 is shown having an embossed bottom and second core 118 is shown having an embossed top. The embossed top of second core 118 and the embossed bottom of first core 116 provide increased longitudinal flow while reducing lateral flow, and, in this manner, reducing leakage. Said another way, the embossed top of second core 118 and the embossed bottom of first core 116 allows fluid to move longitudinally towards the front and the back of a wearer, as opposed to towards the legs of a wearer.

Each of the first core 116 and the second core 118 may be composed of any materials suitable for absorbing the fluids and discharge including, but not limited to, a fibrous material (e.g., fluffed wood pulp), a super absorbent polymer ("SAP"), or the combination of SAP and fibrous material. The SAP can be natural or synthetic and may be biodegradable. Non-limiting examples of SAP include polymers based on acrylate(s) such as sodium acrylate, potassium acrylate, and/or an alkyl acrylate(s) (e.g., methyl acrylate, ethyl acrylate, propyl acrylate, butyl acrylate, and hexyl acrylate). The absorbency of the diaper may vary depending upon whether it is intended for use by infants, children and/or adults.

While FIGS. 3 and 4 depict the first core 116 having an embossed bottom, and the second core 118 having an embossed top, in some embodiments, an absorbent article can have only a single core with no embossing, a single core with embossing on both, and/or other combinations of one or two cores each with embossing on one, both, or neither side. While the figures show absorbent articles include one or two cores, in some embodiments, absorbent articles can include more or fewer cores.

FIGS. 3 and 4 depict embossing as including four spaced apart embossing "lines," in some embodiments. However, a core can include more or fewer embossing lines. In some embodiments, embossing lines can be adjacent one another, or can be a combination of adjacent and space apart embossing line. In this manner, the different combinations of embossing lines can define an embossing pattern. While FIGS. 3 and 4 depict embossing substantially along the entire width and length of each respective core, in some embodiments a core can have embossing substantially along an entire width and/or length, and/or a portion of a width and/or length.

In embodiments of the invention, the first 116 and second 118 cores may be created with or without the use of super absorbent polymer (SAP). While some literature indicates that the presence of SAP in a diaper used for urine testing is considered benign, manufacturing diapers without SAP for the benefit of accuracy is contemplated by the present invention and may be considered beneficial.

Returning to FIGS. 1 and 2, the absorbent article 100 may further include a set of leak guards and/or a set leg cuffs 142, 144, both known to those of ordinary skill in the art. Additionally, the exemplary absorbent article includes an outer layer or backsheet 135 and elastic bands 137. The elastic bands 137 can by used to gather the leg of the article around the user's leg, improving the fit of the absorbent article 100 and can improve the comfort of the wearer. Elastic bands and other elastic materials may be used at other places in the absorbent article in order to improve the fit and/or fluid retention of the article.

In further embodiments of the invention, the absorbent article includes a sensor system. The sensor system may function to sense a level of wetness and provide a means of measuring that wetness. The sensor system may comprise two metal strips 162 placed between the topsheet 130 and backsheet 135 of the diaper. The strips 162 may be placed adjacent a top surface of the backsheet 135 below the absorbent core 116.

Both the dimension of the strips and distance between the strips are calculated to provide appropriate and uniform resistance changes when they become wet with urine. The saline urine forms a resistive link between the strips of metal and this resistance is input into a comparator circuit to produce an appropriate output. The metal used may be aluminum because of its cost and ease and variety of manufacture. However, any metal capable of sensing and providing a changing resistance could be also used. In addition to metal, any conductive fiber that provide the same function could be used, including for example, a combination stainless steel and nylon thread in a sewn application. The metal strips 162 may include a Mylar support backing to provide additional strength during manufacture and application.

Figure 5:
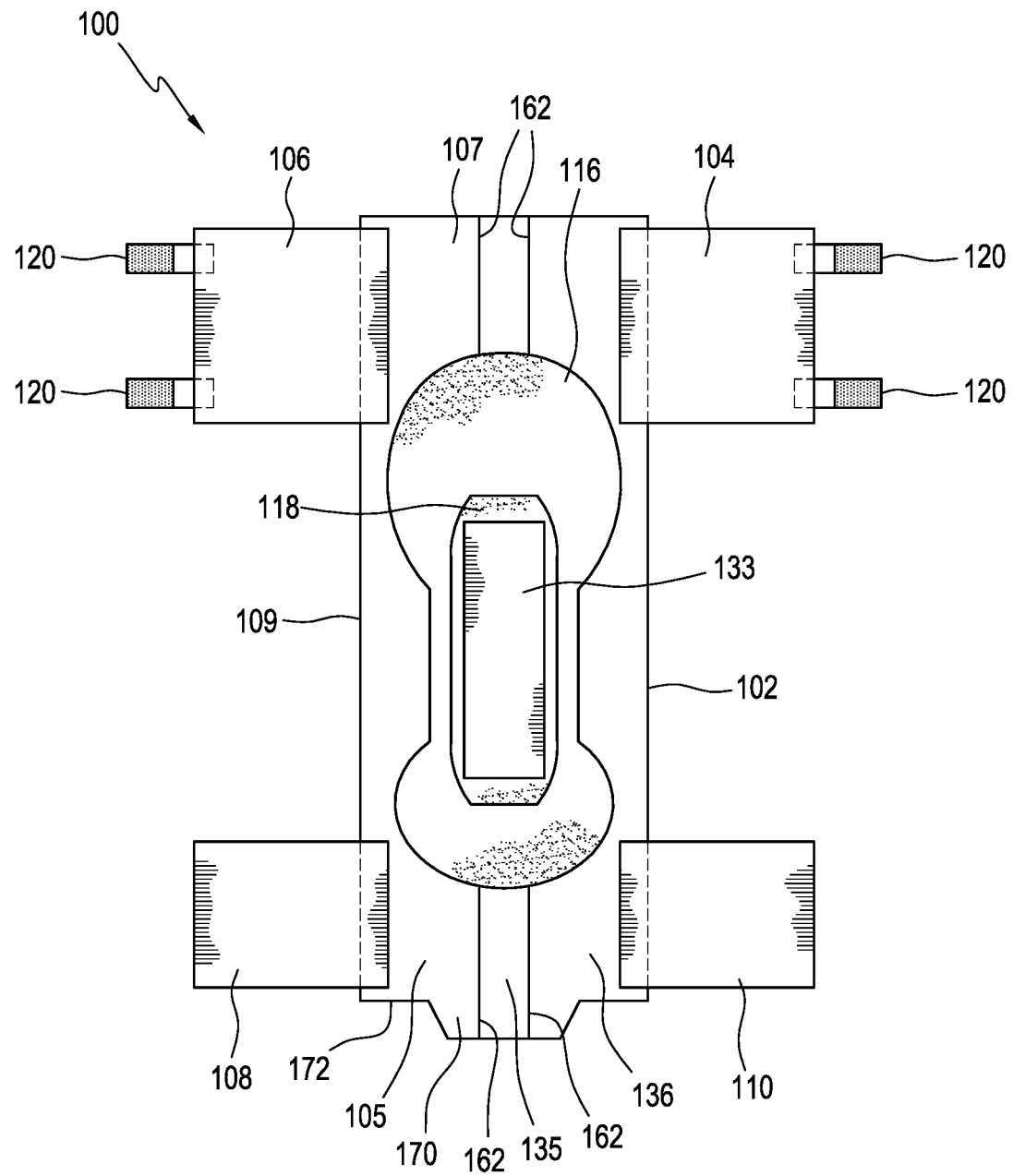
FIG. 5 is a top plan view of an absorbent article in a substantially flat un-contracted position according to a further embodiment of the invention.

As illustrated in FIG. 5, a front portion 105 of the diaper chassis 102 may have a tab 170 that extends beyond the front edge 172 of the diaper. The tab 170 may be formed by an extension of the backsheet 135 or may be a separate portion. The strips 162 extend onto the tab 170. Alternatively, the tab may be formed at a back portion 107 of the diaper.

Figure 6:
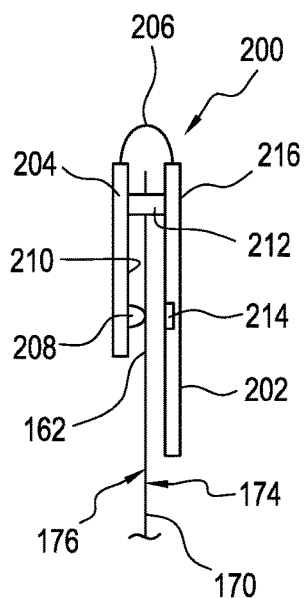
FIG. 6 is a schematic side view of an indicator device of a sensor system in accordance with an embodiment of the invention.
Figure 7:
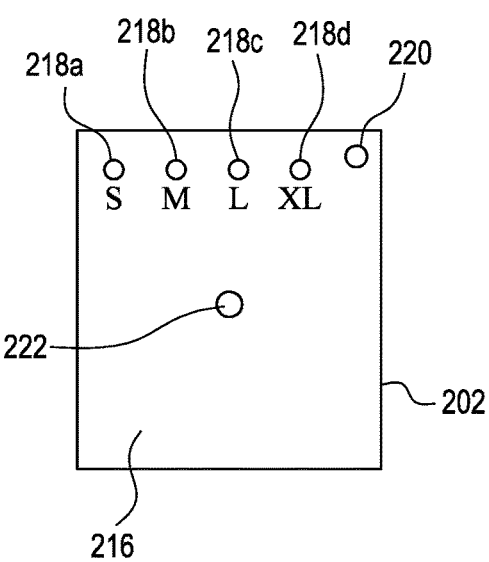
FIG. 7 is a view of a front surface of an outer housing of the indicator device depicted in FIG. 6.
Figure 8:
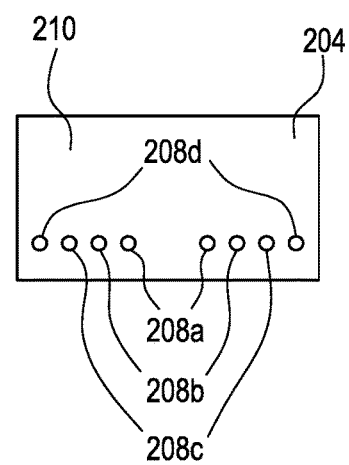
FIG. 8 is a view of an inner housing of the indicator device depicted in FIG. 6.

As illustrated in FIGS. 6-8, the sensor system may further comprise an indicator device 200, which may be in the form of a clip or other means of securing a sensor to a disposable article. FIG. 6 shows a cross sectional view of the diaper tab portion 170, having an inner surface 174 and an outer surface 176. The indicator device 200 may be attached to the tab 170 and include an outer housing 202, and inner housing 204 and a hinge portion 206. Alternatively, the indicator device may be attached to another portion of the diaper such as the back portion 107 or front portion 105 if the diaper does not have tab 170.

Pins 208 may extend from the inner housing 204 to contact strips 162 that extend onto the tab 170. Alternatively, the pins may extend from the outer housing 202. For example, the outer housing 202 may include a PC board with the pins extending slightly through the back of the PC board, such that when they are soldered they will form pin prick contact points. The contact points will penetrate an outside surface 174 of the tab 170 and will contact the strips 162. Holes 214 may be formed on the opposite housing to the pins 208 such that the pins pass through the tab 170 and into the holes. In alternative embodiments, pins 208 will pass through the tab 170 and into recesses, slots indentations or other appropriate structures on the surface of the opposite housing. Wires may connect pins 208 with electronic components positioned within the outer housing 202.

A fastener 212 may extend between the inner 202 and outer 204 housings. The fastener serves to secure the housings to the diaper tab and prevent removal of the indicator device 200. The fastener 212 may pass through the tab 170, such as a pin, rivet or other penetrating fastener. Alternatively, the fastener may only engage the inner 176 and outer 174 surfaces of the tab without penetrating the tab, such as a snap. The fastener may be a separate piece or may be integrally formed with the inner and outer housings. The hinge 206 of the indicator device allows the indicator device to be placed over the tab with the inner housing 204 on the inside of the diaper and the outer housing 202 on the outside. The fastener 212 then secures the indicator device in place. A hole may be preformed in the tab 170 corresponding to the position of the fastener 212 to aid in proper placement of the indicator device 200.

Figure 9:
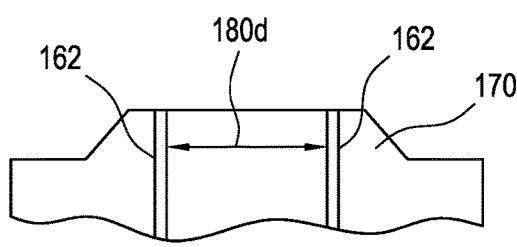
FIG. 9 is a view of spacing between sensor strips of an embodiment of the invention.
Figure 10:
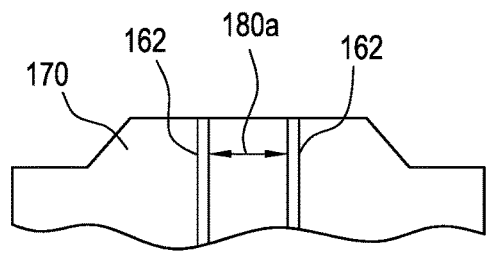
FIG. 10 is a view of alternative spacing between sensor strips of an embodiment of the invention.

FIG. 8 shows the surface 210 of the inside housing 204 that is adjacent to the tab 170. Pins 208 may be formed in spaced pairs 208a, 208b, 208c, 208d. The pin pairs may each consist of single pins or may be made up of groups, clusters or columns of pins. As shown in FIGS. 9-10, the spacing between the strips 162 may vary depending on the size of the diaper. For example, FIG. 9 show an extra large ("XL") diaper with a first strip spacing 180d, while FIG. 10 illustrates a small ("S") diaper with a second strip spacing 180a. This spacing may correspond to the spacing between the pairs of pins 208. For example, spacing 180d of the XL diaper will correspond to the spacing between the outer pair of pins 208d, while the spacing 180a of the S diaper will correspond to the spacing between the inner pair of pins

208a. In this manner, the sensor system will be able to distinguish the size of diaper depending which pair of pins 208 contacts the strips 162.

FIG. 7 shows a front face 216 of the outer housing 202. The housing may include a first indicator light 220. The light may illuminate to indicate that the indicator device has been properly attached to the diaper and the pins 208 have made contact with the strips 162. The indicator device 200 may also emit an audible acknowledgment indicator (a "beep") to indicate that the indicator device has been properly attached. The indicator device 200 may also emit a second audible indicator, different from the acknowledgment indicator, to indicate that the indicator device has not been properly attached. The outer housing 202 may also include a number of indicator lights 218a-d. The indicator lights may correspond and including indicia indicating small, medium, large or extra-large diaper sizes. For example, if the indicator device 200 is attached to the diaper shown in FIG. 9, the pin pair 208d will make contact with the strips 162 spaced apart by distance 180d. The corresponding indicator light 218d on the outer housing 202 will illuminate, indicating that the indicator device has been applied to an extra-large diaper. Alternatively, if the indicator device 200 is attached to the diaper shown in FIG. 10, the pin pair 208a will make contact with the strips 162 spaced apart by distance 180a. The corresponding indicator light 218a on the outer housing 202 will illuminate, indicating that the indicator device has been applied to a small diaper. As illustrated, the indicator device covers a range sizes including S, M, L and XL. However, those skilled in the art will recognize that the indicator lights may correspond and include a narrower or wider range of sizes and size combinations. For example, the indicator device may include additional pins 208 and indicator lights 218 corresponding to additional adult sizes XXL, XXXL, bariatric sizes or various child sizes.

The indicator lights 218 may illuminate automatically upon attachment of the indicator device 200. Alternatively, the front face 216 of the outer housing 202 may include a button 222 or other actuator means to actuate the lights 218. The button 222 may also be configured so that actuating the button allows the caregiver to cycle through the different available sizes with the appropriate light activating when the cycle reaches the size to which the indicator device has been attached. In further embodiments, the outer housing 202 of the indicator device may include a switch, such as a toggle switch, that moves a pair of pins to the spacing that corresponds with the spacing of the desire brief size. In this manner, the pins 208 will only connect to strips 162 and illuminate indicator lights 218, 220 if the indicator device is placed on a diaper of the desired size.

Upon attachment to the diaper, the indicator device may also transmit information regarding the diaper size to a remote display device. The remote display device may be a software application ("app") running on a mobile electronic device, such as a mobile phone or similar. The app may display the size of diaper to which the indicator device has been attached. The app may also compare the size of diaper to which the indicator device has been attached with data entered regarding the intended size for the patient and thereby verify that the size of diaper that has been put on the patient is the size of diaper that should have been used for the patient. The app may include a visual or audible acknowledgement to indicate the correct diaper size has been used.

Figure 11:
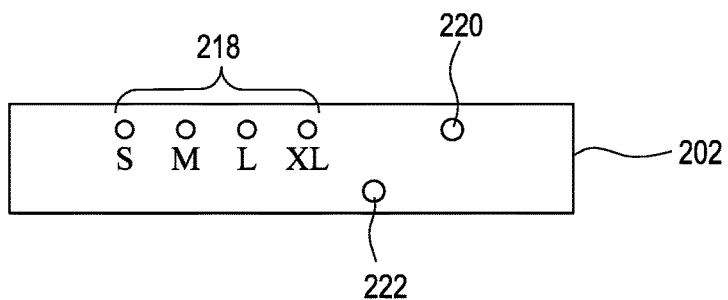
FIG. 11 is a view of a front surface of an outer housing of a further embodiment of the indicator device depicted in FIG. 6.

The indicator device 200 may be sized and configured as appropriate for its function and the comfort of the patient. For example, the outer housing 202 may be generally square shaped as shown in FIG. 7. Alternatively, the housing 202 may be made significantly wider than it is long, as shown in FIG. 11, or longer than it is wide. The housings 202, 204 may also include padding or cushioning to reduce discomfort or ulcer causing pressure points. In FIGS. 6-8 and 11, the housings 202, 204 are illustrated as rigid housings having significant thickness. However, one or both of the housings may be formed with only sufficient thickness to include the necessary elements. The housings may consist simply of printed circuit boards without any enclosing structure. The housings may also be flexible. For example, if pins 208 are made to extend from the outer housing 202, the inner housing 204 may consist only of a flexible piece with sufficient thickness to accommodate the desired fastener 212.

The indicator device 200 may also comprise a magnetically actuated activation and/or locking mechanism. In such a mechanism, a magnetic element is swiped across the outer housing 202 of the indicator device. The magnetic swipe activates the device and moves an internal mechanical locking mechanism that engages and locks fastener 212, thereby preventing the patient from removing the sensor from the diaper.

While the present invention has been described with reference to one or more particular embodiments, those skilled in the art will recognize that many changes may be made thereto without departing from the spirit and scope of the present invention. Furthermore, components from one embodiment can be used in other non-exclusive embodiments. Each of these embodiments and obvious variations thereof is contemplated as falling within the spirit and scope of the invention.

What is claimed is:

1. A sensor for connecting to absorbent articles, the sensor comprising:
    a housing that is positioned adjacent to a surface of an absorbent article;
    a plurality of first contacts that extend from the housing, wherein the first contacts are spaced apart a first distance and each contact electrically connects with one of a plurality of contact strips embedded in a first absorbent article and spaced apart the first distance when the sensor is connected to the first absorbent article;
    a plurality of second contacts that extend from the housing, wherein the second contacts are spaced apart a second distance and each contact electrically connects with one of a plurality of contact strips embedded in a second absorbent article and spaced apart the second distance when the sensor is connected to the second absorbent article;
    wherein the second distance is greater than the first distance.

2. The sensor of claim 1 wherein the housing comprises an inner housing that is positioned adjacent to an inner surface of the absorbent article.

3. The sensor of claim 2 wherein the housing further comprises an outer housing that is positioned adjacent to an outer surface of the absorbent article.

4. The sensor of claim 3 wherein the housing further comprises a hinge portion connecting the inner housing with the outer housing.

5. The sensor of claim 1 wherein the contacts of the plurality of first contacts and the plurality of second contacts comprise pins that penetrate a surface of the absorbent article.

6. The sensor of claim 5 wherein the plurality of first contacts comprises a pair of single pins.

7. The sensor of claim 5 wherein the plurality of first contacts comprises a pair of groups of multiple pins, wherein the groups of pins are spaced apart the first distance.

8. The sensor of claim 7 wherein the groups of pins are organized into clusters.

9. The sensor of claim 7 wherein the groups of pins are organized into lines.

10. The sensor of claim 1 further comprising an indicator that provides information indicating that the plurality of first contacts has electrically connected with the plurality of contact strips.

11. The sensor of claim 10 wherein the indicator provides information regarding the size of the absorbent article.

12. The sensor of claim 1 further comprising an indicator that provides information indicating that the plurality of second contacts has electrically connected with the plurality of contact strips.

13. The sensor of claim 1 further comprising a transmitter that transmits information to a remote display device.

14. The sensor of claim 13 wherein the transmitted information comprises information regarding the size of the absorbent article.

15. A sensor for use in conjunction with a system of absorbent articles comprising a first absorbent article having a first pair of contact strips embedded in the first article and spaced apart a first distance and a second absorbent article having a second pair of contact strips embedded in the second article and spaced apart a second distance that is greater than the first distance, the sensor comprising:

a housing that is positioned adjacent to a surface of an absorbent article;

a pair of first contacts that extend from the housing, wherein the first contacts are spaced apart the first distance and each contact electrically connects with one of the first pair of contact strips embedded in a first absorbent article when the sensor is connected to the first absorbent article;

a pair of second contacts that extend from the housing, wherein the second contacts are spaced apart the second distance and each contact electrically connects with one of a second pair of contact strips embedded in a second absorbent article when the sensor is connected to the second absorbent article.

16. The sensor of claim 15 wherein each contact comprises a pin.

17. The sensor of claim 15 wherein each contact comprises a group of pins.

18. The sensor of claim 15 further comprising an indicator that provides information indicating that the pair of first contacts has electrically connected with the first pair of contact strips or that the pair of second contacts has electrically connected with the second pair of contact strips.

19. The sensor of claim 18 wherein the indicator provides information indicating that the absorbent article has a first size when the pair of first contacts has electrically connected with the first pair of contact strips and provides information indicating that the absorbent article has a second size when the pair of second contacts has electrically connected with the second pair of contact strips.

20. The sensor of claim 15 wherein the housing comprises an inner housing and an outer housing and further comprising a lock that connects the inner housing and the outer housing capturing a portion of the absorbent article between the inner housing and outer housing.

* * * * *